United States Patent [19]

Ackermann et al.

[11] Patent Number: 5,322,853
[45] Date of Patent: Jun. 21, 1994

[54] MICROBICIDAL BENZOTRIAZOLE COMPOUNDS

[75] Inventors: Peter Ackermann, Pfeffingen; Max Schellenbaum, Muttenz, both of Switzerland

[73] Assignee: Ciba-Geigy Corporation, Ardsley, N.Y.

[21] Appl. No.: 52,313

[22] Filed: Apr. 23, 1993

Related U.S. Application Data

[60] Division of Ser. No. 931,884, Aug. 18, 1992, abandoned, which is a continuation of Ser. No. 717,751, Jun. 19, 1991, abandoned.

[30] Foreign Application Priority Data

Jun. 21, 1990 [CH] Switzerland ............... 2065/90

[51] Int. Cl.$^5$ ............... A01N 43/647; C07D 249/18
[52] U.S. Cl. ............... 514/359; 548/259
[58] Field of Search ............... 548/259; 514/359

[56] References Cited

U.S. PATENT DOCUMENTS

| | | | |
|---|---|---|---|
| 2,943,017 | 6/1960 | Sasse et al. | 167/33 |
| 4,622,323 | 11/1986 | Giraudeu et al. | 514/228 |
| 4,734,427 | 3/1988 | Riebel et al. | 514/398 |

FOREIGN PATENT DOCUMENTS

| | | |
|---|---|---|
| 178708 | 4/1986 | European Pat. Off. |
| 355049 | 2/1990 | European Pat. Off. |
| 367242 | 5/1990 | European Pat. Off. |
| 3406011 | 8/1985 | Fed. Rep. of Germany |

OTHER PUBLICATIONS

Chem. Abst. 114:6515r-Barton (1991).

*Primary Examiner*—Patricia L. Morris
*Attorney, Agent, or Firm*—George R. Dohmann

[57] ABSTRACT

Novel benzotriazolesulfonic acid derivatives of formula

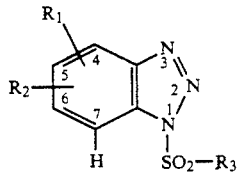

wherein:

$R_1$ is hydrogen, halogen, $C_1$–$C_4$alkyl, $C_1$–$C_4$alkoxy, $C_1$–$C_4$haloalkoxy having at least two identical or different halogen atoms, $CF_3$, nitro or the group $N(R')R''$, wherein $R'$ and $R''$ are each independently of the other $C_1$–$C_4$alkyl;

$R_2$ is phenoxy or phenylthio each of which is unsubstituted or mono- to tri-substituted by halogen, $C_1$–$C_4$alkyl, $C_1$–$C_4$alkoxy, $C_1$–$C_4$haloalkoxy having at least two identical or different halogen atoms, cyano, nitro, $C_2$–$C_4$alkenyl, $C_2$–$C_4$alkynyl, phenyl, 2-phenylethynyl or by a further phenoxy radical that is unsubstituted or substituted by halogen, $C_1$–$C_4$alkyl and/or by $C_1$–$C_4$alkoxy; or $R_2$ is the radical O—CH$_2$—O;

$R_3$ is alkyl, aryl or aralkyl having a maximum of 14 carbon atoms, these radicals can be substituted by halogen, $C_1$–$C_4$alkyl and/or by nitro;

including the position isomers of $R_1$ and $R_2$, insofar as those substituents occupy positions 5 and 6.

The novel compounds have plant-protecting properties and are suitable especially for protecting plants against attack by phytopathogenic microorganisms such as fungi, especially Oomycetes.

25 Claims, No Drawings

MICROBICIDAL BENZOTRIAZOLE COMPOUNDS

This application is a divisional of Ser. No. 07/931,884, filed Aug. 18, 1992, now abandoned, which is a continuation of Ser. No. 07/717,751, filed Jun. 19, 1991, now abandoned.

The present invention relates to novel benzotriazole-sulfonic acid derivatives of the following formula I. It relates furthermore to the preparation of those compounds and to agrochemical compositions that comprise at least one of those compounds as active ingredient. The invention also relates to the preparation of the said compositions and to the use of the compounds or compositions for controlling or preventing an attack on plants by phytopathogenic microorganisms, especially fungi.

The compounds according to the invention correspond to the general formula I

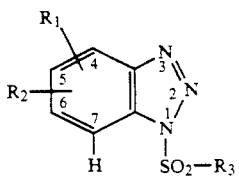

wherein:
- $R_1$ is hydrogen, halogen, $C_1$–$C_4$alkyl, $C_1$–$C_4$alkoxy, $C_1$–$C_4$haloalkoxy having at least two identical or different halogen atoms, $CF_3$, nitro or the group $N(R')R''$, wherein $R'$ and $R''$ are each independently of the other $C_1$–$C_4$alkyl;
- $R_2$ is phenoxy or phenylthio each of which is unsubstituted or mono- to tri-substituted by halogen, $C_1$–$C_4$alkyl, $C_1$–$C_4$alkoxy, $C_1$–$C_4$haloalkoxy having at least two identical or different halogen atoms, cyano, nitro, $C_2$–$C_4$alkenyl, $C_2$–$C_4$alkynyl, phenyl, 2-phenylethynyl or by a further phenoxy radical that is unsubstituted or substituted by halogen, $C_1$–$C_4$alkyl and/or by $C_1$–$C_4$alkoxy; or $R_2$ is the radical O—CH$_2$—O;
- $R_3$ is alkyl, aryl or aralkyl having a maximum of 14 carbon atoms, these radicals can be substituted by halogen, $C_1$–$C_4$alkyl and/or by nitro;

including the position isomers of $R_1$ and $R_2$, insofar as those substituents occupy positions 5 and 6.

Depending on the number of carbon atoms indicated, alkyl on its own or as a component of another substituent, such as alkoxy or haloalkoxy etc., is to be understood as being, for example, the following straight-chain or branched groups: methyl, ethyl, propyl, butyl and their isomers, for example isopropyl, isobutyl, tert-butyl etc. Halogen and halo are fluorine, chlorine, bromine or iodine. Haloalkoxy is therefore a mono-to perhalogenated alkoxy radical, for example $OCH_2F$, $OCHF_2$, $OCHFCH_3$, $OCH_2CH_2Br$, $OCF_2CHFCl$ etc. $C_2$–$C_4$alkenyl is an unsaturated aliphatic radical having one or more double bonds, for example propen-1-yl, allyl, buten-1-yl, buten-2-yl, buten-3-yl, etc. Alkynyl is to be understood as being unsaturated aliphatic radicals having a maximum of 4 carbon atoms, for example propargyl, butyn-2-yl, butyn-3-yl etc. Aryl and aralkyl are, for example, phenyl, benzyl, phenethyl, naphthyl etc.

The compounds of formula I are oils or solids that are stable at room temperature and are distinguished by valuable microbicidal properties. They can be used preventively and curatively in the agricultural sector or related fields for controlling plant-destructive microorganisms. The compounds of formula I according to the invention are, when used at low concentrations, distinguished not only by excellent microbicidal, especially fungicidal, activity, but also by especially good plant tolerability.

The following groups of compounds are preferred on account of their pronounced plant-protecting properties:

Compounds of formula I wherein:

1a)

$R_1$ is hydrogen, halogen, $C_1$–$C_4$alkyl, methoxy, ethoxy, $CF_3$, $NO_2$, $C_1$–$C_2$haloalkoxy having at least two fluorine atoms, diethylamine or dimethylamine;

and $R_2$ and $R_3$ are as defined for formula I.

1b)

$R_1$ is hydrogen, fluorine, chlorine, bromine, methyl, ethyl, methoxy, $CF_3$, $NO_2$, $C_1$–$C_2$haloalkoxy having at least 2 fluorine atoms, or dimethylamine;

and $R_2$ and $R_3$ are as defined for formula I.

1c)

$R_1$ is hydrogen, chlorine, bromine, methyl, methoxy, $CF_3$, $NO_2$, trifluoromethoxy, trifluorochloroethoxy, difluoromethoxy or dimethylamine;

and $R_2$ and $R_3$ are as defined for formula I.

1d)

$R_1$ is chlorine, methyl, methoxy, $CF_3$ or dimethylamine;

and $R_2$ and $R_3$ are as defined for formula I.

2a)

$R_2$ is phenoxy or phenylthio each of which is unsubstituted or mono-or di-substituted by fluorine, chlorine, bromine, $C_1$–$C_4$alkyl, $C_1$–$C_4$alkoxy, $C_1$–$C_2$haloalkoxy having at least 2 fluorine atoms, nitro, cyano, allyl, propargyl, 2-phenylethynyl or by a further phenoxy radical that is unsubstituted or substituted by fluorine, chlorine, bromine or by methyl;

and $R_1$ and $R_3$ are as defined for formula I.

2b)

$R_2$ is phenoxy that is unsubstituted or substituted by fluorine, chlorine, bromine, $C_1$–$C_4$alkyl, $C_1$–$C_4$alkoxy, $C_1$–$C_2$haloalkoxy having at least 2 fluorine atoms, cyano, nitro, allyl, propargyl, 2-phenylethynyl or by a further phenoxy radical that is unsubstituted or substituted by fluorine, chlorine, bromine or by methyl;

and $R_1$ and $R_3$ are as defined for formula I.

2c)

$R_2$ is phenylthio that is unsubstituted or substituted by fluorine, chlorine, $C_1$–$C_2$alkyl, $C_1$–$C_2$alkoxy, $C_1$–$C_2$haloalkoxy having at least 2 fluorine atoms, nitro, allyl, propargyl or by 2-phenylethynyl;

and $R_1$ and $R_3$ are as defined for formula I.

2d)

$R_2$ is phenoxy that is unsubstituted or substituted by chlorine, bromine, methyl, tert-butyl, methoxy, ethoxy, trifluoromethoxy, cyano, nitro, allyl, propargyl, 2-phenylethynyl or by a further phenoxy radical that is unsubstituted or substituted by fluorine, bromine or by methyl;

and $R_1$ and $R_3$ are as defined for formula I.

3a)

$R_3$ is $C_1$-$C_4$alkyl; $C_1$-$C_4$alkyl substituted by halogen; phenyl; phenyl substituted by halogen, $C_1$-$C_4$alkyl and/or by nitro; benzyl; or benzyl substituted by halogen, $C_1$-$C_4$alkyl and/or by nitro;

and $R_1$ and $R_2$ are as defined for formula I.

3b)

$R_3$ is $C_1$-$C_4$alkyl; $C_1$-$C_4$alkyl substituted by fluorine or by chlorine; phenyl; phenyl substituted by chlorine, methyl or by nitro; benzyl; or benzyl substituted by chlorine, methyl or by nitro;

and $R_1$ and $R_2$ are as defined for formula I.

4a)

$R_1$ is hydrogen, halogen, $C_1$-$C_4$alkyl, methoxy, ethoxy, $CF_3$, $NO_2$, $C_1$-$C_2$haloalkoxy having at least 2 fluorine and/or 2 chlorine atoms, diethylamine or dimethylamine;

$R_2$ is phenoxy or phenylthio each of which is unsubstituted or mono-or di-substituted by fluorine, chlorine, bromine, $C_1$-$C_4$alkyl, $C_1$-$C_4$alkyl, $C_1$-$C_4$alkoxy, $C_1$-$C_2$haloalkoxy having at least 2 fluorine atoms, cyano, nitro, allyl, propargyl, 2-phenylethynyl or by a further phenoxy radical that is unsubstituted or substituted by fluorine, chlorine, bromine or by methyl; and $R_3$ is $C_1$-$C_4$alkyl; $C_1$-$C_4$alkyl substituted by halogen; phenyl; phenyl substituted by halogen, $C_1$-$C_4$alkyl and/or by nitro; benzyl; or benzyl substituted by halogen, $C_1$-$C_4$alkyl and/or by nitro.

4b $R_1$ is hydrogen, fluorine, chlorine, bromine, methyl, ethyl, methoxy, $CF_3$, $NO_2$, $C_1$-$C_2$haloalkoxy having at least 2 fluorine atoms, or dimethylamine;

$R_2$ is phenoxy that is unsubstituted or substituted by fluorine, chlorine, bromine, $C_1$-$C_4$alkyl, $C_1$-$C_4$alkoxy, $C_1$-$C_2$haloalkoxy having at least 2 fluorine atoms, cyano, nitro, allyl, propargyl, 2-phenylethynyl or by a further phenoxy radical that is unsubstituted or substituted by fluorine, bromine or by methyl; and $R_3$ is $C_1$-$C_4$alkyl; $C_1$-$C_4$alkyl substituted by fluorine or by chlorine; phenyl; phenyl substituted by chlorine, methyl or by nitro; benzyl; or benzyl substituted by chlorine, methyl or by nitro.

4c)

$R_1$ is hydrogen, chlorine, bromine, methyl, methoxy, $CF_3$, $NO_2$, trifluoromethoxy, trifluorochloroethoxy, difluoromethoxy or dimethylamine;

$R_2$ is phenylthio that is unsubstituted or substituted by fluorine, chlorine, $C_1$-$C_2$alkyl, $C_1$-$C_2$alkoxy, $C_1$-$C_2$haloalkoxy having at least 2 fluorine atoms, nitro, allyl, propargyl or by 2-phenylethynyl; and $R_3$ is $C_1$-$C_4$alkyl; $C_1$-$C_4$alkyl substituted by fluorine or by chlorine; phenyl; phenyl substituted by chlorine, methyl or by nitro; benzyl; or benzyl substituted by chlorine, methyl or by nitro.

4d)

$R_1$ is chlorine, methyl, methoxy, $CF_3$ or dimethylamine;

$R_2$ is phenoxy that is unsubstituted or substituted by chlorine, bromine, methyl, tert-butyl, methoxy, ethoxy, trifluoromethoxy, cyano, nitro, allyl, propargyl, 2-phenylethynyl or by a further phenoxy radical that is unsubstituted or substituted by fluorine, bromine or by methyl; and $R_3$ is $C_1$-$C_4$alkyl; $C_1$-$C_4$alkyl substituted by fluorine or by chlorine; phenyl; phenyl substituted by chlorine, methyl or by nitro; benzyl; or benzyl substituted by chlorine, methyl or by nitro.

Compounds of formula I preferred for their mode of action are as follows:

1-N-methanesulfonyl-5-chloro-6-phenoxy-benzotriazole;

1-N-methanesulfonyl-5-chloro-6-(2-chlorophenoxy)-benzotriazole;

1-N-methanesulfonyl-5-chloro-6-(4-chlorophenoxy)-benzotriazole;

1-N-methanesulfonyl-5-chloro-6-(2,4-dibromophenoxy)-benzotriazole;

1-N-methanesulfonyl-5-chloro-6-(2-fluorophenoxy)-benzotriazole;

1-N-methanesulfonyl-5-chloro-6-(4-ethoxyphenoxy)-benzotriazole;

3-N-methanesulfonyl-5-chloro-6-phenoxy-benzotriazole;

3-N-methanesulfonyl-5-chloro-6-(2-chlorophenoxy)-benzotriazole;

3-N-methanesulfonyl-5-chloro-6-(4-chlorophenoxy)-benzotriazole;

3-N-methanesulfonyl-5-chloro-6-(2,4-dibromophenoxy)-benzotriazole;

3-N-methanesulfonyl-5-chloro-6-(2-fluorophenoxy)-benzotriazole; and

3-N-methanesulfonyl-5-chloro-6-(4-ethoxyphenoxy)-benzotriazole;

and mixtures of the 1-N- and 3-N-substituted structural isomers. The compounds of formula I are prepared .

1) by reacting a compound of formula II

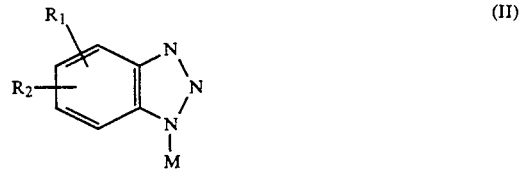

(II)

with a compound of formula III $$Q-SO_2-R_3 \quad (III),$$

wherein $R_1$, $R_2$ and $R_3$ are as defined for formula I and M is hydrogen or an alkali metal, preferably sodium, potassium or lithium, and Q is a halogen atom, preferably chlorine, or the radical $O-SO_2-R_3$, in an inert solvent, in the presence or absence of a base, at temperatures from $-30°$ to $180°$ C., preferably from $-10°$ to $80°$ C., under normal, reduced or elevated pressure, preferably normal pressure; or 2) by diazotizing a compound of formula IV

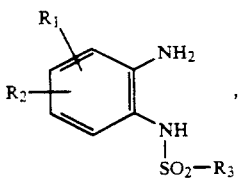

wherein $R_1$, $R_2$ and $R_3$ are as defined for formula I, either a) with an inorganic nitrite in a solvent, preferably in water or in a mixture of water with an alcohol, preferably methanol or ethanol, or in a mixture of water with an ether, preferably dioxane or dimethoxyethane, in the presence of an acid, at temperatures from −30° to 180° C., preferably from 0° to 80° C.; or b) with an organic nitrite, preferably ethyl nitrite, amyl nitrite or tert-butyl nitrite, in a solvent, preferably an alcohol, such as methanol or ethanol, or an ether, such as dioxane or dimethoxyethane, in the presence or absence of an acid, at temperature from −30° to 180° C., preferably from 0° to 80° C., under normal pressure or elevated pressure.

Compounds of formula IIa

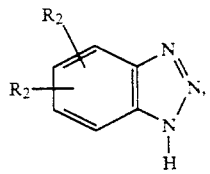

wherein:

$R_1$ is hydrogen, halogen, $C_1$–$C_4$alkyl, $C_1$–$C_4$alkoxy, $C_1$–$C_4$haloalkoxy having at least two identical or different halogen atoms, $CF_3$, nitro or the group $N(R')R''$, wherein $R'$ and $R''$ are each independently of the other $C_1$–$C_4$alkyl;

$R_2$ is phenoxy or phenylthio each of which is unsubstituted or mono-to tri-substituted by halogen, $C_1$–$C_4$alkyl, $C_1$–$C_4$alkoxy, $C_1$–$C_4$haloalkoxy having at least two identical or different halogen atoms, cyano, nitro, $C_2$–$C_4$alkenyl, $C_2$–$C_4$alkynyl, phenyl, 2-phenylethynyl or by a further phenoxy radical that is unsubstituted or substituted by halogen, $C_1$–$C_4$alkyl and/or by $C_1$–$C_4$alkoxy;

$R_3$ is alkyl, aryl or aralkyl having a maximum of 14 carbon atoms, these radicals can be substituted by halogen, $C_1$–$C_4$alkyl and/or by nitro;

are novel with the exception of those compounds in which, simultaneously, $R_1$ is hydrogen and $R_2$ is 5-(2-chloro4-trifluoromethylphenoxy) or $R_1$ is 6-chlorine and $R_2$ is 5-phenoxy.

The compounds of formula IIa are prepared 3) by diazotizing a compound of formula V

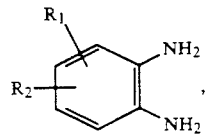

wherein $R_1$ and $R_2$ are as defined for formula IIa, either 3a) with an inorganic nitrite in a solvent, preferably in water or in a mixture of water with an alcohol, preferably methanol or ethanol, or in a mixture of water with an ether, preferably dioxane or dimethoxyethane, in the presence of an acid, at temperatures from −30° to 180° C., preferably from 0° to 80° C.; or 3b) with an organic nitrite, preferably ethyl nitrite, amyl nitrite or tert-butyl nitrite, in a solvent, preferably an alcohol, such as methanol or ethanol, or an ether, such as dioxane or dimethoxyethane, in the presence or absence of an acid, at temperatures from −30° to 180° C., preferably from 0° to 80° C., under normal pressure or elevated pressure; or 4) by reacting a compound of formula VI

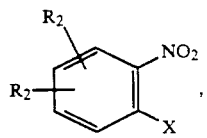

wherein $R_1$ and $R_2$ are as defined for formula IIa and X is a halogen atom, preferably fluorine or chlorine, with hydrazine or hydrazine hydrate in a solvent, preferably an alcohol, such as methanol or ethanol, in the presence of an acidbinding agent, preferably sodium carbonate, potassium carbonate or triethylamine, at the reflux temperature of the reaction medium, to form a compound of formula VII

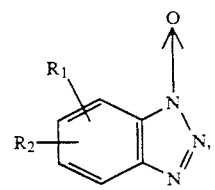

which is then reacted with a chloroketone of formula VIII $$Cl-CH_2-CO-(C_1-C_6alkyl) \qquad (VIII),$$

preferably chloroacetone, in an inert solvent in the presence of a base, at temperatures from 40° to 140° C., preferably from 60° to 120° C.

The following inert solvents are suitable for the processes described above: aliphatic, cycloaliphatic or aromatic hydrocarbons, for example hexane, cyclohexane, toluene, xylene, petroleum ether or ligroin; chlorinated hydrocarbons, for example methylene chloride, chloroform, carbon tetrachloride, chlorobenzene; ethers, for example diethyl ether, diisopropyl ether, furan, tetrahydrofuran, dioxane; ketones, for example acetone, methyl ethyl ketone; alcohols, for example methanol, ethanol, isopropanol; esters, for example ethyl acetate, butyl acetate; nitriles, for example acetonitrile, propionitrile; acid amides, for example dimethylformamide; sulfones and sulfoxide, for example dimethyl sulfoxide, sulfolane.

Suitable bases or acid-binding agents are, for example, hydroxides, carbonates, hydrogen carbonates or alcoholates of alkali metals; and also tertiary amines, for example, triethylamine, triisopropylamine, pyridine or 4-N,N-dimethylaminopyridine.

The above-described processes correspond to methods of synthesis that are known from the literature. They are described, for example, in Chem. Reviews 46, 1 (1950) and in German Offenlegungsschrift 34 06 011.

The synthesis of starting compounds of the type of formula IV is known from U.S. Pat. No. 2,943,017.

Compounds with benzotriazolesulfonic acid structures are already known. Such compounds are described in DE-1 046 937, GB-885 843 and U.S. Pat. No. 2,943,017 as active ingredients that can be used as fungicides.

The known compounds, however, are not always able satisfactorily to meet the requirements currently made of them as fungicides in practice, in particular when used at low rates of application and against certain pests.

Surprisingly, it has been found that the compounds of formula I have, for practical field application purposes, a very advantageous biocidal spectrum for the control of phytopathogenic microorganisms, especially fungi. They have very advantageous curative, preventive and, in particular, systemic properties and are used for protecting numerous cultivated plants.

The novel compounds of formula I have proved effective against specific genera of the fungus class Fungi imperfecti (e.g. Cercospora), Basidiomycetes (e.g. Puccinia) and also Ascomycetes (e.g. Erysiphe and Venturia) and in particular against Oomycetes (e.g. Plasmopara and Phytophthora). In the field of plant protection they therefore represent a valuable addition to compositions for controlling phytopathogenic fungi. For practical field application purposes they advantageously exhibit curative and preventive and also systemic properties and can be used for protecting numerous cultivated plants. With these compounds it is possible to inhibit or destroy the pests which occur on plants or on parts of plants (fruit, blossoms, leaves, stems, tubers, roots) in different crops of useful plants, while at the same time the parts of plants which grow later are also protected, for example, against phytopathogenic fungi. The compounds of formula I can also be used as dressing agents for protecting seeds (fruit, tubers, grains) and plant cuttings against fungus infections as well as against phytopathogenic fungi which occur in the soil.

The invention also relates to compositions comprising as active ingredient compounds of formula I, especially plant-protecting compositions, and to their use in the agricultural sector or related fields.

The present invention further embraces the preparation of those compositions, which comprises homogeneously mixing the active ingredient with one or more compounds or groups of compounds described herein. The invention furthermore relates to a method of treating plants, which comprises applying thereto the novel compounds of formula I or the novel compositions.

Target crops to be protected within the scope of the present invention comprise e.g. the following species of plants: cereals (wheat, barley, rye, oats, rice, maize, sorghum and related crops); beet (sugar beet and fodder beet); pomes, drupes and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (cucumber, marrows, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocados, cinnamon, camphor) or plants such as tobacco, nuts, coffee, sugar cane, tea, peppers, vines, hops, bananas and natural rubber plants, as well as ornamentals.

The compounds of formula I are normally applied in the form of compositions and can be applied to the crop area or plant to be treated, simultaneously or in succession, with further compounds. These further compounds can be fertilisers or micronutrient donors or other preparations that influence plant growth. They can also be selective herbicides, insecticides, fungicides, bactericides, nematicides, molluscicides or mixtures of several of these preparations, if desired together with further carriers, surfactants or other application-promoting adjuvants customarily employed in formulation technology.

Suitable carriers and adjuvants can be solid or liquid and correspond to the substances ordinarily employed in formulation technology, e.g. natural or regenerated mineral substances, solvents, dispersants, wetting agents, tackifiers, thickeners, binders or fertilisers.

A preferred method of applying a compound of formula I, or an agrochemical composition which comprises at least one of said compounds, is foliar application. The number of applications and the rate of application depend on the risk of infestation by the corresponding pathogen. However, the compounds of formula I can also penetrate the plant through the roots via the soil (systematic action) if the locus of the plant is impregnated with a liquid formulation, or if the compounds are applied in solid form to the soil, e.g. in granular form (soil application). In paddy rice crops, such granules may be applied in metered amounts to the flooded rice field. The compounds of formula I may, however, also be applied to seeds (coating) either by impregnating the seeds with a liquid formulation comprising a compound of formula I, or coating them with a solid formulation.

The compounds of formula I are used in unmodified form or, preferably, together with the adjuvants conventionally employed in formulation technology and are for this purpose advantageously formulated in known manner e.g. into emulsifiable concentrates, coatable pastes, directly sprayable or dilutable solutions, dilute emulsions, wettable powders, soluble powders, dusts, granules and also encapsulations in e.g. polymer substances. As with the nature of the compositions, the methods of application, such as spraying, atomising, dusting, scattering, coating or pouring, are chosen in accordance with the intended objectives and the prevailing circumstances. Advantageous rates of application are normally from 10 g to 5 kg of active ingredient (a.i.) per ha, preferably from 20 g to 1 kg a.i./ha.

The formulations, i.e. the compositions, preparations or mixtures comprising the compound (active ingredient) of formula I and, where appropriate, a solid or liquid adjuvant, are prepared in known manner, e.g. by homogeneously mixing and/or grinding the active ingredients with extenders, e.g. solvents, solid carriers and, where appropriate, surfaceactive compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils, such as epoxidised coconut oil or soybean oil; or water.

The solid carriers use e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are, for example, calcite or sand. In addition, a great number of pregranulated materials of inorganic nature can be used, e.g. especially dolomite or pulverised plant residues.

Depending on the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Both so-called water-soluble soaps and water-soluble synthetic surface-active compounds are suitable anionic surfactants.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyllaurin salts.

More frequently, however, so-called synthetic surfactants are used, especially alkanesulfonates, fatty alcohol sulfates, sulfonated benzimidazole derivatives or alkylarylsulfonates.

The fatty alcohol sulfonates or sulfates are usually in the form of alkali metal salts, alkaline earth metal salts or unsubstituted or substituted ammonium salts and contain a $C_8$–$C_{22}$alkyl radical, which also includes the alkyl moiety of acyl radicals, e.g. the sodium or calcium salt of lignosulfonic acid, of dodecyl sulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde.

Also suitable are corresponding phosphates, e.g. salts of the phosphoric acid ester of an adduct of p-nonylphenol with 4 to 14 mol of ethylene oxide.

Non-ionic surfactants are preferably polyglycol ether derivatives of aliphatic or cycloaliphatic alcohols, saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethyleneethanol, polyethylene glycol and octylphenoxypolyethoxyethanol.

Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methyl sulfates or ethyl sulfates, e.g. stearyltrimethylammonium chloride or benzyldi(2-chloroethyl)ammonium bromide.

Further surfactants customarily employed in formulation technology are known to the person skilled in the art or can be taken from the relevant specialist literature.

The agrochemical compositions usually comprise 0.1 to 99% by weight, preferably 0.1 to 95% by weight, of a compound of formula I, 99.9 to 1% by weight, preferably 99.9 to 5% by weight, of a solid or liquid adjuvant, and 0 to 25% by weight, preferably 0.1 to 25% by weight, of a surfactant.

Whereas commercial products will preferably be formulated as concentrates, the end user will normally employ dilute formulations.

The compositions may also comprise further auxiliaries such as stabilisers, antifoams, viscosity regulators, binders, tackifiers as well as fertilisers or other active ingredients for obtaining special effects.

The following Examples serve to illustrate the invention in greater detail, without limiting it.

1. PREPARATION EXAMPLES

1.1 Preparation of 5-(2,3-dichlorophenoxy)-4-chloro-2nitroaniline

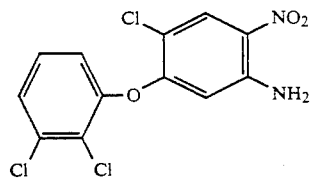

A mixture of 171 g of 2,3-dichlorophenol and 186 g of 4,5-dichloro-2-nitroaniline is heated to 150° C. 101 g of a 50% potassium hydroxide solution are added dropwise to the dark-red liquid over a period of 1 hour. The water of reaction formed is distilled off with a small amount of phenol. The reaction mixture is stirred overnight at 150° C. and then, at that temperature, 450 ml of dimethylformamide are added. The solution is allowed to cool and is all poured onto a mixture of 3 l of water and 150 ml of concentrated sodium hydroxide solution. The greenish suspension is stirred at room temperature for 1 hour, and the crystals that form are filtered off and washed neutral with water and then dried. The still moist yellowish crystals are used in crude form in the next reaction step.

1.2 Preparation of 4-chloro-5-(2,3-dichlorophenoxy)-ophenylenediamine

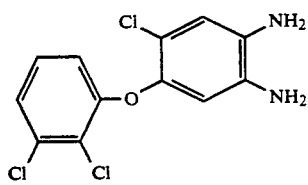

17 ml of glacial acetic acid are added dropwise over a period of 80 minutes to a suspension of 80 g of iron powder in 400 ml of water and the mixture is then heated to reflux temperature. After the addition of 100 ml of chlorobenzene, the nitroaniline prepared in Example 1.1 is added to the reaction mixture over a period of 2 hours. During the course of this addition an exothermic reaction is observed. After heating at reflux for 14 hours the reduction of the nitro group is complete. The mixture is allowed to cool, diluted with 500 ml of chlorobenzene and the aqueous phase is rendered alkaline with sodium carbonate solution. The organic phase is removed, dried with sodium sulfate and concentrated under reduced pressure. After the addition of 100 ml of petroleum ether to the crude product, a crystalline mass is obtained which is filtered off and washed with petroleum ether, yielding the title compound having a melting point of 110°–112° C.

1.3 Preparation of 5-chloro-6-(2,3-dichlorophenoxy)benzotriazole

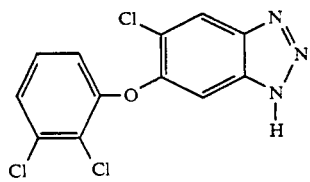

7.5 g of diamine prepared in Example 1.2 are suspended in 50 ml of water and, at room temperature, 2.9 ml of acetic acid are added. After heating briefly to 60° C., the reaction solution is cooled to 5° C. and, at that temperature, a solution of 3.9 g of sodium nitrite in 12 ml of water is added. The mixture is then heated at 80° C. for 3 hours, and the brown suspension is cooled and filtered. The crystals obtained are recrystallised twice from ethanol/water, yielding the title compound having a melting point of 173° C.

1.4 Preparation of the isomeric mixture of 1-N-(methanesulfonyl)- and 3-N-(methanesulfonyl)-5-chloro-6-(2,3dichlorophenoxy)-benzotriazole

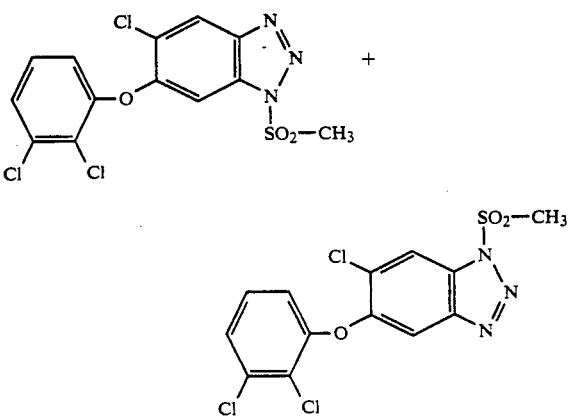

3.1 g of benzotriazole from Example 1.3 are dissolved in 30 ml of dimethylformamide and 2.78 ml of triethylamine. 1.56 ml of methanesulfonyl chloride are added dropwise to the brown solution without external heating, in the course of which the temperature rises to 45° C. The mixture is then stirred at room temperature for one hour and the suspension is poured into 500 ml of water. The white product that precipitates is filtered off and recrystallised from ethanol, yielding the desired product in the form of an isomeric mixture having a melting point of 178°–180° C.

TABLE 1

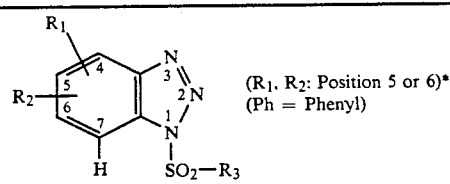

($R_1$, $R_2$: Position 5 or 6)*
(Ph = Phenyl)

| Comp. No. | $R_1$ | $R_2$ | $R_3$ | Physical data |
|---|---|---|---|---|
| 1.1 | Cl | O—Ph | $CH(CH_3)_2$ | |
| 1.2 | $CH_3$ | O—Ph | $C_2H_5$ | |
| 1.3 | Cl | O—Ph | $CH_3$ | m.p. 100–104° C. |
| 1.4 | $CH_3$ | O—Ph | $CH_3$ | |
| 1.5 | $CH_3$ | O—Ph | $CH(CH_3)_2$ | |
| 1.6 | Cl | O—Ph-2-Cl | $CH_3$ | m.p. 152–154° C. |
| 1.7 | Cl | O—Ph-2-Cl | $C_2H_5$ | |
| 1.8 | Cl | O—Ph-2-Cl | $C_6H_5$ | |
| 1.9 | Cl | O—Ph-3-Cl | $CH_3$ | m.p. 76–79° C. |
| 1.10 | Cl | O—Ph-4-Cl | $C_3H_7(n)$ | |
| 1.11 | Cl | O—Ph-4-Cl | $CH_2$—Ph | |
| 1.12 | Cl | O—Ph-4-Cl | $C_6H_5$ | |
| 1.13 | Cl | O—Ph-4-Cl | $CH_3$ | m.p. 144–145° C. |
| 1.14 | Cl | O—Ph-2-F | $CH_3$ | m.p. 132–133° C. |
| 1.15 | Cl | O—Ph-2-Br | $C_4H_9$ | |
| 1.16 | Cl | O—Ph-2,4-$(Br)_2$ | $CH_3$ | m.p. 147–148° C. |
| 1.17 | $CH_3$ | O—Ph-4-Cl | $CH_3$ | |

TABLE 1-continued

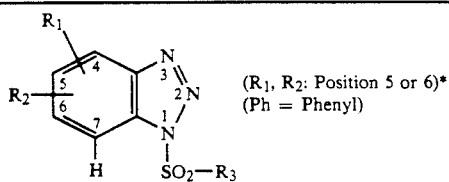

($R_1$, $R_2$: Position 5 or 6)*
(Ph = Phenyl)

| Comp. No. | $R_1$ | $R_2$ | $R_3$ | Physical data |
|---|---|---|---|---|
| 1.18 | $OCF_3$ | O—Ph-2-Cl | $CH_3$ | |
| 1.19 | $NO_2$ | O—Ph | $C_6H_5$ | |
| 1.20 | $NO_2$ | O—Ph-4-Cl | $CH_3$ | |
| 1.21 | $C_4H_9$ | O—Ph-4-C($CH_3$)$_3$ | $C_3H_7$(n) | |
| 1.22 | $C_4H_9$ | S—Ph | $CH_3$ | |
| 1.23 | N($CH_3$)$_2$ | O—Ph-4-Cl | $CH_3$ | |
| 1.24 | N($CH_3$)$_2$ | O—Ph-2-F | $CH_3$ | |
| 1.25 | N($CH_3$)$_2$ | S—Ph-4-Cl | $CH_3$ | |
| 1.26 | CN | O—Ph-4-Cl | $CH_3$ | |
| 1.27 | $OCF_2CFHCF_3$ | O—Ph-4-Cl | $CH_3$ | |
| 1.28 | O—$CF_2CFClH$ | S—Ph-4-Cl | $CH_3$ | |
| 1.29 | O—$CF_2CFClH$ | S—Ph-4-Cl | CH($CH_3$)$_2$ | |
| 1.30 | Cl | O—Ph-4-$OC_2H_5$ | $CH_3$ | m.p. 164–166° C. |
| 1.31 | Cl | O—Ph-4-O—Ph | $CH_3$ | m.p. 161–163° C. |
| 1.32 | Cl | O—Ph-4-(O—Ph-4-F) | $CH_3$ | |
| 1.33 | Cl | O—Ph-4—Ph | $CH_3$ | m.p. 200–205° C. |
| 1.34 | Cl | O—Ph-4—Ph | CH($CH_3$)$_3$ | |
| 1.35 | Cl | O—Ph-4-(O—Ph-4-$CH_3$) | $CH_3$ | |
| 1.36 | Cl | O—Ph-4-(C≡C—Ph) | $CH_3$ | |
| 1.37 | Cl | O—Ph-4-Allyl | $CH_3$ | |
| 1.38 | Cl | O—Ph-3,5-(Cl)$_2$ | $CH_3$ | m.p. 143–145° C. |
| 1.39 | Cl | O—Ph-2,3-($CH_3$)$_2$ | $CH_3$ | m.p. 140–144° C. |
| 1.40 | Cl | O—Ph-2,3-(Cl)$_2$ | CH($CH_3$)$_2$ | m.p. 95–98° C. |
| 1.41 | Cl | O—Ph-2,3-(Cl)$_2$ | $C_3H_7$(n) | m.p. 94–96° C. |
| 1.42 | Cl | O—Ph-2,3-(Cl)$_2$ | $C_6H_5$ | m.p. 115–118° C. |
| 1.43 | Cl | O—Ph-2,3-(Cl)$_2$ | Ph-4-$CH_3$ | m.p. 134–137° C. |
| 1.44 | Cl | O—Ph-2,3-(Cl)$_2$ | Ph-4-$NO_2$ | m.p. 172–175° C. |
| 1.45 | Cl | O—Ph-2,3-(Cl)$_2$ | Ph-4-Cl | m.p. 130–132° C. |
| 1.46 | Cl | S—Ph-4-Cl | $CH_3$ | m.p. 135–138° C. |
| 1.47 | Cl | S—Ph-4-$CH_3$ | $CH_3$ | |
| 1.48 | Cl | O—Ph-2,4-(F)$_2$ | $CH_3$ | |
| 1.49 | Cl | O—Ph-2-Cl-4-F | $CH_3$ | m.p. 191–193° C. |
| 1.50 | Cl | O—Ph-3-$NO_2$ | $CH_3$ | |
| 1.51 | Cl | O—Ph-2-$NO_2$-4-Cl | $CH_3$ | |
| 1.52 | Cl | O—Ph-4-$OCF_3$ | $CH_3$ | |
| 1.53 | $CH_3$ | O—Ph-3-$OC_2H_5$ | $CH_3$ | |
| 1.54 | $CH_3$ | O—Ph-4-CN | $CH_3$ | |
| 1.55 | Cl | O—Ph-2,3-(Cl)$_2$ | $CH_2$—Ph | |
| 1.56 | Cl | O—Ph-2,3-(Cl)$_2$ | $CH_2CF_3$ | |
| 1.57 | Cl | O—Ph-2,3-(Cl)$_2$ | $CH_3$ | m.p. 178–180° C. |
| 1.58 | Cl | O—Ph-2,3-(Cl)$_2$ | $C_2H_5$ | |
| 1.59 | Cl | O—Ph-4-F | $CH_3$ | m.p. 114–116° C. |
| 1.60 | Cl | O—Ph-4-$CH_3$ | $CH_3$ | m.p. 165° C. |
| 1.61 | Cl | O—Ph-3,4-($CH_3$)$_2$ | $CH_3$ | m.p. 152° C. |
| 1.62 | Cl | O—Ph-3-$CF_3$ | $CH_3$ | m.p. 109° C. |
| 1.63 | Cl | O—Ph-3,5-($CH_3$)$_2$ | $CH_3$ | m.p. 150° C. |
| 1.64 | Cl | S—Ph | $CH_3$ | m.p. 138–140° C. |
| 1.65 | Cl | S—Ph-4-C($CH_3$)$_3$ | $CH_3$ | m.p. 128° C. |
| 1.66 | Cl | O—Ph-4-$C_2H_5$ | $CH_3$ | m.p. 153° C. |
| 1.67 | Cl | O—Ph-2,4-(Cl)$_2$ | $CH_3$ | m.p. 187–189° C. |
| 1.68 | Cl | S—Ph-2,5-(Cl)$_2$ | $CH_3$ | m.p. 200–204° C. |
| 1.69 | Cl | O—Ph-3-$OCF_3$ | $CH_3$ | m.p. 149–151° C. |
| 1.70 | Cl | O—Ph-3,4-($CH_3$)$_2$ | $CF_3$ | m.p. 95° C. |
| 1.71 | Cl | S—Ph-4-F | $CH_3$ | m.p. 140–151° C. |
| 1.72 | Cl | O—Ph-4-CN | $CH_3$ | m.p. 158–160° C. |
| 1.73 | Cl | O—Ph-2,4-($CH_3$)$_2$ | $CH_3$ | m.p. 188–190° C. |
| 1.74 | Cl | O—Ph-4-Cl | $CF_3$ | m.p. 76–78° C. |
| 1.75 | Cl | O—Ph-3,5-($CH_3$)$_2$ | $CF_3$ | m.p. 112° C. |
| 1.76 | Cl | O—Ph-4-$CH_3$ | $CF_3$ | m.p. 122° C. |
| 1.77 | Cl | O—Ph-2,4-(Cl)$_2$ | $CF_3$ | oil |
| 1.78 | Cl | S—Ph-4-C($CH_3$)$_3$ | $CF_3$ | m.p. 119° C. |
| 1.79 | Cl | S—Ph-4-C($CH_3$)$_3$ | Ph | m.p. 131° C. |
| 1.80 | Cl | O—Ph-2-F | $CF_3$ | m.p. 113° C. |
| 1.81 | Cl | O—Ph-2,3-(Cl)$_2$ | $CF_3$ | m.p. 107° C. |
| 1.82 | Cl | O—Ph-3-O—Ph | $CH_3$ | m.p. 109–115° C. |
| 1.83 | H | O—Ph-4-$OC_2H_5$ | $CH_3$ | m.p. 50–65° C. |
| 1.84 | H | O—Ph-2-Cl,4-$CF_3$ | $CH_3$ | m.p. 85–96° C. |
| 1.85 | Cl | —O—Ph-3,4($OCH_2O$) | $CH_3$ | m.p. 145–149° C. |
| 1.86 | Cl | —O—Ph-2-$OC_2H_5$ | $CH_3$ | m.p. 147–149° C. |
| 1.87 | Cl | —O—Ph-4-$OCH_3$ | $CH_3$ | m.p. 151–153° C. |
| 1.88 | Cl | —O—Ph-2-$OCH_3$ | $CH_3$ | m.p. 160–165° C. |

TABLE 1-continued

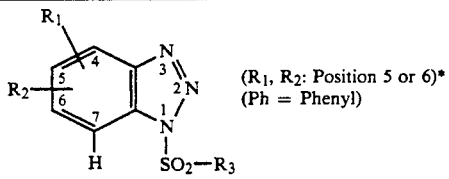

(R₁, R₂: Position 5 or 6)*
(Ph = Phenyl)

| Comp. No. | R$_1$ | R$_2$ | R$_3$ | Physical data |
|---|---|---|---|---|
| 1.89 | Cl | —O—Ph-4-OC$_3$H$_7$(n) | CH$_3$ | m.p. 176–179° C. |
| 1.90 | Cl | —O—Ph-3-OCH$_3$ | CH$_3$ | m.p. 130–131° C. |
| 1.91 | Cl | —O—Ph-3,5-(OCH$_3$)$_2$ | CH$_3$ | m.p. 136–139° C. |
| 1.92 | Cl | —S—Ph-4-OCH$_3$ | CH$_3$ | m.p. 134–138° C. |
| 1.93 | Cl | O—Ph | CF$_3$ | |
| 1.94 | Cl | O—Ph | Ph | |
| 1.95 | Cl | O—Ph-2-Cl | CF$_3$ | |
| 1.96 | Cl | O—PH-2-F | CF$_3$ | |
| 1.97 | Cl | O—Ph-2-F | Ph | |
| 1.98 | Cl | O—Ph-4-Cl | CF$_3$ | |
| 1.99 | Cl | O—Ph-4-F | CF$_3$ | |
| 1.100 | Cl | O—Ph-4-CN | CF$_3$ | |
| 1.101 | Cl | O—Ph-4-OPh | CF$_3$ | |
| 1.102 | Cl | O—Ph-4-OPh | Ph | |
| 1.103 | Cl | O—Ph-4-Ph | CF$_3$ | |
| 1.104 | Cl | O—Ph-4-C(CH$_3$)$_3$ | CH$_3$ | |
| 1.105 | Cl | O—Ph-4-C(CH$_3$)$_3$ | CF$_3$ | |
| 1.106 | Cl | O—Ph-4-C(CH$_3$)$_3$ | Ph | |
| 1.107 | Cl | O—Ph-4-O—CF$_3$ | CF$_3$ | |
| 1.108 | Cl | S—Ph | CF$_3$ | |
| 1.109 | Cl | S—Ph-4-F | CF$_3$ | |
| 1.110 | Cl | O—Ph-3-OPh | CF$_3$ | |
| 1.111 | Cl | O—Ph-2,4-(CH$_3$)$_2$ | CF$_3$ | |
| 1.112 | Cl | O—Ph-2-(n)C$_3$H$_7$ | CH$_3$ | |
| 1.113 | Cl | O—Ph-4-(n)C$_3$H$_7$ | CH$_3$ | |
| 1.114 | Cl | O—Ph-4-CH(CH$_3$)$_3$ | CH$_3$ | |
| 1.115 | Cl | O—Ph-2-CH(CH$_3$)$_2$ | CH$_3$ | |
| 1.116 | Cl | O—Ph-3-CH(CH$_3$)$_2$ | CH$_3$ | |
| 1.117 | Cl | O—Ph-2-CH(CH$_3$)CH$_2$CH$_3$ | CH$_3$ | |
| 1.118 | Cl | O—Ph-4-CH(CH$_3$)CH$_2$CH$_3$ | CH$_3$ | |
| 1.119 | Cl | O—Ph-2-C(CH$_3$)$_3$ | CH$_3$ | |
| 1.120 | Cl | O—Ph-3-C(CH$_3$)$_3$ | CH$_3$ | |
| 1.121 | Cl | O—Ph-2-SCH$_3$ | CH$_3$ | |
| 1.122 | Cl | O—Ph-2-SC$_2$H$_5$ | CH$_3$ | |
| 1.123 | Cl | O—Ph-2-OCH(CH$_3$)$_2$ | CH$_3$ | |
| 1.124 | Cl | O—Ph-4-OC$_4$H$_9$(n) | CH$_3$ | |
| 1.125 | Cl | O—Ph-3-N(C$_2$H$_5$)$_2$ | CH$_3$ | |
| 1.126 | Cl | O—Ph-2,3-(OCH$_3$)$_2$ | CH$_3$ | m.p. 142–143° C. |
| 1.127 | Cl | O—Ph-3-N(CH$_3$)$_2$ | CH$_3$ | |
| 1.128 | Cl | O—Ph-4-SCH$_3$ | CH$_3$ | m.p. 148–150° C. |
| 1.129 | Cl | O—Ph-3,4,5-(OCH$_3$)$_3$ | CH$_3$ | |
| 1.130 | Cl | O—Ph-3-CH$_3$-4-SCH$_3$ | CH$_3$ | m.p. 103–107° C. |
| 1.131* | 5-Cl | 6-(O—Ph-4-OC$_2$H$_5$) | CH$_3$ | m.p. 186° C. |
| 1.132* | 6-Cl | 5-(O—Ph-4-OC$_2$H$_5$) | CH$_3$ | m.p. 161° C. |

*Isomeric mixtures with respect to R$_1$ and R$_2$ in position 5 or 6
*Individual isomers

TABLE 2

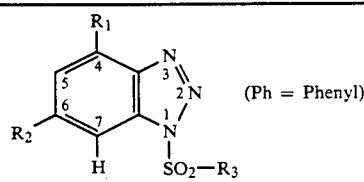

(Ph = Phenyl)

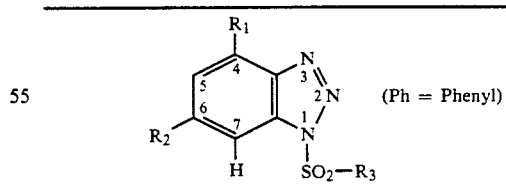

(Ph = Phenyl)

| Comp. No. | R$_1$ | R$_2$ | R$_3$ | Physical data |
|---|---|---|---|---|
| 2.1 | Cl | O—Ph | CH$_3$ | |
| 2.2 | Cl | O—Ph-3-Cl | CH$_3$ | |
| 2.3 | Cl | O—Ph-4-Cl | CH$_3$ | |
| 2.4 | Cl | O—Ph-4-Cl | CH(CH$_3$)$_2$ | |
| 2.5 | CH$_3$ | O—Ph-4-Cl | CH$_3$ | |
| 2.6 | CH$_3$ | O—Ph-2-F | CH$_3$ | |
| 2.7 | CH$_3$ | O—Ph-2,3-(Cl)$_2$ | CH$_3$ | |
| 2.8 | CH$_3$ | O—Ph-4-Cl | CH$_2$—Ph | |
| 2.9 | Cl | O—Ph-2-F | CH$_3$ | |
| 2.10 | Cl | O—Ph-2-Cl | CH$_3$ | |
| 2.11 | Cl | O—Ph-4-Cl | Ph | |
| 2.12 | Cl | O—Ph-4-Cl | CH$_2$—Ph | |
| 2.13 | Br | O—Ph-4-Cl | CH$_3$ | |
| 2.14 | NO$_2$ | O—Ph-4-Cl | CH$_3$ | |
| 2.15 | CF$_3$ | O—Ph-2-Cl | CH$_3$ | |
| 2.16 | OCHF$_2$ | O—Ph-4-Cl | CH$_3$ | |
| 2.17 | Cl | O—Ph-4-(O—Ph-4-F) | CH$_3$ | |
| 2.18 | Cl | O—Ph-4-Ph | CH$_3$ | |

TABLE 2-continued

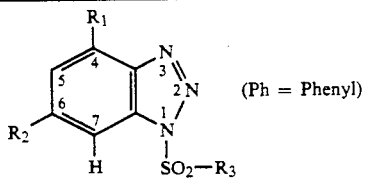
(Ph = Phenyl)

| Comp. No. | R₁ | R₂ | R₃ | Physical data |
|---|---|---|---|---|
| 2.19 | Br | O—Ph-4-Ph | CH₃ | |
| 2.20 | Br | O—Ph-4-(O—Ph-4-F) | CH₃ | |
| 2.21 | Br | O—Ph-3-O—Ph | CH₃ | |
| 2.22 | Cl | O—Ph-4-Cl | Ph-4-CH₃ | |
| 2.23 | Cl | O—Ph-4-OC₂H₅ | CH₃ | |
| 2.24 | Cl | O—Ph-4-OCH₃ | CH₃ | |
| 2.25 | Cl | O—Ph-3,5-(OCH₃)₂ | CH₃ | |
| 2.26 | CH₃ | O—Ph-4-O—Ph | CH₃ | |
| 2.27 | F | O—Ph-2-F | CH₃ | |
| 2.28 | H | O—Ph-4-Cl | CH₃ | |
| 2.29 | H | S—Ph-2-Cl | CH₃ | |
| 2.30 | H | O—Ph-4-OCH₃ | CH₃ | |
| 2.31 | H | O—Ph-4-O—Ph | CH₃ | |
| 2.32 | H | O—Ph-2-Cl-4-F | CH₃ | |
| 2.33 | H | O—Ph-3-Cl | C₆H₅ | |
| 2.34 | H | O—Ph | CH(CH₃)₃ | |
| 2.35 | H | S—Ph | CH₃ | |
| 2.36 | H | O—Ph-4-O—Ph | CH₃ | |
| 2.37 | H | O—Ph-2,3-(Cl)₂ | CH₃ | |
| 2.38 | Cl | —O—Ph-4-CH₃ | CH₃ | |
| 2.39 | Cl | —O—Ph-4-NO₂ | CH₃ | |
| 2.40 | Cl | —S—Ph-4-Cl | CH₃ | |
| 2.41 | Cl | —S—Ph-4-OCH₃ | CH₃ | |
| 2.42 | Cl | —S—Ph | CH₃ | |
| 2.43 | Cl | —O—Ph-2,4-Cl₂ | CH₃ | |
| 2.44 | Cl | —O—Ph-2,3-Cl₂ | CH₃ | |
| 2.45 | Cl | —O—Ph-2,3-(CH₃)₂ | CH₃ | |
| 2.46 | Cl | —O—Ph-4-F | CH₃ | |
| 2.47 | Cl | —O—Ph-4-CH₃ | CH₃ | |
| 2.48 | Cl | —O—Ph-2-Cl,4-F | CH₃ | |
| 2.49 | Cl | —O—Ph-2,4-(CH₃)₂ | CH₃ | |
| 2.50 | Cl | —S—Ph-4-F | CH₃ | |

TABLE 3

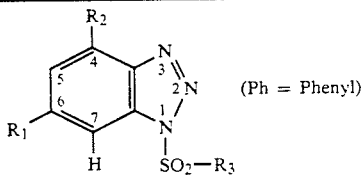
(Ph = Phenyl)

| Comp. No. | R₁ | R₂ | R₃ | Physical data |
|---|---|---|---|---|
| 3.1 | Cl | O—Ph | CH₃ | |
| 3.2 | Cl | O—Ph-3-Cl | CH₃ | |
| 3.3 | Cl | O—Ph-4-Cl | CH₃ | |
| 3.4 | Cl | O—Ph-4-Cl | CH(CH₃)₂ | |
| 3.5 | CH₃ | O—Ph-4-Cl | CH₃ | |
| 3.6 | CH₃ | O—Ph-2-F | CH₃ | |
| 3.7 | CH₃ | O—Ph-2,3-(Cl)₂ | CH₃ | |
| 3.8 | CH₃ | O—Ph-4-Cl | CH₂—Ph | |
| 3.9 | Cl | O—Ph-2-F | CH₃ | |
| 3.10 | Cl | O—Ph-2-Cl | CH₃ | |
| 3.11 | Cl | O—Ph-4-Cl | Ph | |
| 3.12 | Cl | O—Ph-4-Cl | CH₂—Ph | |
| 3.13 | Br | O—Ph-4-Cl | CH₃ | |
| 3.14 | NO₂ | O—Ph-4-Cl | CH₃ | |
| 3.15 | CF₃ | O—Ph-2-Cl | CH₃ | |
| 3.16 | OCHF₂ | O—Ph-4-Cl | CH₃ | |
| 3.17 | Cl | O—Ph-4-(O—Ph-4-F) | CH₃ | |
| 3.18 | Cl | O—Ph-4-Ph | CH₃ | |
| 3.19 | Br | O—Ph-4-Ph | CH₃ | |
| 3.20 | Br | O—Ph-4-(O—Ph-4-F) | CH₃ | |
| 3.21 | Br | O—Ph-3-O—Ph | CH₃ | |
| 3.22 | Cl | O—Ph-4-Cl | Ph-4-CH₃ | |
| 3.23 | Cl | O—Ph-4-OC₂H₅ | CH₃ | |

TABLE 3-continued

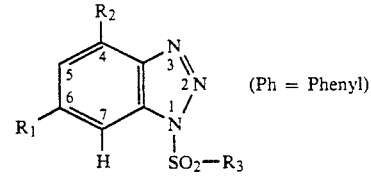
(Ph = Phenyl)

| Comp. No. | R₁ | R₂ | R₃ | Physical data |
|---|---|---|---|---|
| 3.24 | Cl | O—Ph-4-OCH₃ | CH₃ | |
| 3.25 | Cl | O—Ph-3,5-(OCH₃)₂ | CH₃ | |
| 3.26 | CH₃ | O—Ph-4-O—Ph | CH₃ | |
| 3.27 | F | O—Ph-2-F | CH₃ | |
| 3.28 | H | O—Ph-4-Cl | CH₃ | |
| 3.29 | H | S—Ph-2-Cl | CH₃ | |
| 3.30 | H | O—Ph-4-OCH₃ | CH₃ | |
| 3.31 | H | O—Ph-4-O—Ph | CH₃ | |
| 3.32 | H | O—Ph-2-Cl-4-F | CH₃ | |
| 3.33 | H | O—Ph-3-Cl | C₆H₅ | |
| 3.34 | H | O—Ph | CH(CH₃)₃ | |
| 3.35 | H | S—Ph | CH₃ | |
| 3.36 | H | O—Ph-4-Ph | CH₃ | |
| 3.37 | H | O—Ph-2,3-(Cl)₂ | CH₃ | |
| 3.38 | Cl | —O—Ph-4-CH₃ | CH₃ | |
| 3.39 | Cl | —O—Ph-4-NO₂ | CH₃ | |
| 3.40 | Cl | —S—Ph-4-Cl | CH₃ | |
| 3.41 | Cl | —S—Ph-4-OCH₃ | CH₃ | |
| 3.42 | Cl | —S—Ph | CH₃ | |
| 3.43 | Cl | —O—Ph-2,4-Cl₂ | CH₃ | |
| 3.44 | Cl | —O—Ph-2,3-Cl₂ | CH₃ | |
| 3.45 | Cl | —O—Ph-2,3-(CH₃)₂ | CH₃ | |
| 3.46 | Cl | —O—Ph-4-F | CH₃ | |
| 3.47 | Cl | —O—Ph-4-CH₃ | CH₃ | |
| 3.48 | Cl | —O—Ph-2-Cl,4-F | CH₃ | |
| 3.49 | Cl | —O—Ph-2,4-(CH₃)₂ | CH₃ | |
| 3.50 | Cl | —S—Ph-4-F | CH₃ | |

TABLE 4

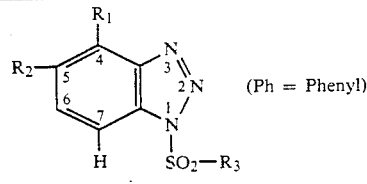
(Ph = Phenyl)

| Comp. No. | R₁ | R₂ | R₃ | Physical data |
|---|---|---|---|---|
| 4.1 | Cl | O—Ph | CH₃ | |
| 4.2 | Cl | O—Ph-3-Cl | CH₃ | |
| 4.3 | Cl | O—Ph-4-Cl | CH₃ | m.p. 140-142° C. |
| 4.4 | Cl | O—Ph-4-Cl | CH(CH₃)₂ | |
| 4.5 | CH₃ | O—Ph-4-Cl | CH₃ | |
| 4.6 | CH₃ | O—Ph-2-F | CH₃ | |
| 4.7 | CH₃ | O—Ph-2,3-(Cl)₂ | CH₃ | |
| 4.8 | CH₃ | O—Ph-4-Cl | CH₂—Ph | |
| 4.9 | Cl | O—Ph-2-F | CH₃ | |
| 4.10 | Cl | O—Ph-2-Cl | CH₃ | |
| 4.11 | Cl | O—Ph-4-Cl | Ph | |
| 4.12 | Cl | O—Ph-4-Cl | CH₂—Ph | |
| 4.13 | Br | O—Ph-4-Cl | CH₃ | |
| 4.14 | NO₂ | O—Ph-4-Cl | CH₃ | |
| 4.15 | CF₃ | O—Ph-2-Cl | CH₃ | |
| 4.16 | OCHF₂ | O—Ph-4-Cl | CH₃ | |
| 4.17 | Cl | O—Ph-4-(O—Ph-4-F) | CH₃ | |
| 4.18 | Cl | O—Ph-4-Ph | CH₃ | |
| 4.19 | Br | O—Ph-4-Ph | CH₃ | |
| 4.20 | Br | O—Ph-4-(O—Ph-4-F) | CH₃ | |
| 4.21 | Br | O—Ph-3-O—Ph | CH₃ | |
| 4.22 | Cl | O—Ph-4-Cl | Ph-4-CH₃ | |
| 4.23 | Cl | O—Ph-4-OC₂H₅ | CH₃ | |
| 4.24 | Cl | O—Ph-4-OCH₃ | CH₃ | m.p. 130° C. |
| 4.25 | Cl | O—Ph-3,5-(OCH₃)₂ | CH₃ | |

TABLE 4-continued

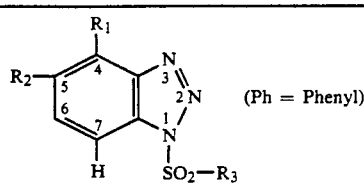
(Ph = Phenyl)

| Comp. No. | R₁ | R₂ | R₃ | Physical data |
|---|---|---|---|---|
| 4.26 | CH₃ | O—Ph-4-(O—Ph) | CH₃ | |
| 4.27 | F | O—Ph-2-F | CH₃ | |
| 4.28 | H | O—Ph-4-Cl | CH₃ | |
| 4.29 | H | S—Ph-2-F | CH₃ | |
| 4.30 | H | O—Ph-4-OCH₃ | CH₃ | |
| 4.31 | H | O—Ph-4-O—Ph | CH₃ | |
| 4.32 | H | O—Ph-2-Cl-4-F | CH₃ | |
| 4.33 | H | O—Ph-3-Cl | C₆H₅ | |
| 4.34 | H | O—Ph | CH(CH₃)₃ | |
| 4.35 | H | S—Ph | CH₃ | |
| 4.36 | H | O—Ph-4-O—Ph | CH₃ | |
| 4.37 | H | O—Ph-2,3-(Cl₂)₂ | CH₃ | |
| 4.38 | H | O—Ph-4-OC₂H₅ | CH₃ | m.p. 133-135° C. |
| 4.39 | Cl | —O—Ph-4-CH₃ | CH₃ | |
| 4.40 | Cl | —S—Ph-4-NO₂ | CH₃ | |
| 4.41 | Cl | —S—Ph-4-Cl | CH₃ | |
| 4.42 | Cl | —S—Ph-4-OCH₃ | CH₃ | |
| 4.43 | Cl | —S—Ph | CH₃ | |
| 4.44 | Cl | —O—Ph-2,4-Cl₂ | CH₃ | |
| 4.45 | Cl | —O—Ph-2,3-Cl₂ | CH₃ | |
| 4.46 | Cl | —O—Ph-2,3-(CH₃)₂ | CH₃ | |
| 4.47 | Cl | —O—Ph-4-F | CH₃ | |
| 4.48 | Cl | —O—Ph-4-CH₃ | CH₃ | |
| 4.49 | Cl | —O—Ph-2-Cl.4-F | CH₃ | |
| 4.50 | Cl | —O—Ph-2,4-(CH₃)₂ | CH₃ | |
| 4.51 | Cl | —S—Ph-4-F | CH₃ | |

TABLE 5

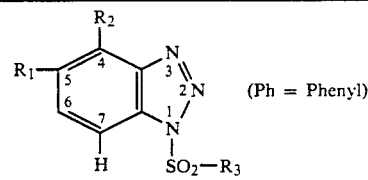
(Ph = Phenyl)

| Comp. No. | R₁ | R₂ | R₃ | Physical data |
|---|---|---|---|---|
| 5.1 | Cl | O—Ph | CH₃ | |
| 5.2 | Cl | O—Ph-3-Cl | CH₃ | |
| 5.3 | Cl | O—Ph-4-Cl | CH₃ | |
| 5.4 | Cl | O—Ph-4-Cl | CH(CH₃)₂ | |
| 5.5 | CH₃ | O—Ph-4-Cl | CH₃ | |
| 5.6 | CH₃ | O—Ph-2-F | CH₃ | |
| 5.7 | CH₃ | O—Ph-2,3-(Cl)₂ | CH₃ | |
| 5.8 | CH₃ | O—Ph-4-Cl | CH₂—Ph | |
| 5.9 | Cl | O—Ph-2-F | CH₃ | |
| 5.10 | Cl | O—Ph-2-Cl | CH₃ | |
| 5.11 | Cl | O—Ph-4-Cl | Ph | |
| 5.12 | Cl | O—Ph-4-Cl | CH₂—Ph | |
| 5.13 | Br | O—Ph-4-Cl | CH₃ | |
| 5.14 | NO₂ | O—Ph-4-Cl | CH₃ | |
| 5.15 | CF₃ | O—Ph-2-Cl | CH₃ | |
| 5.16 | OCHF₂ | O—Ph-4-Cl | CH₃ | |
| 5.17 | Cl | O—Ph-4-(O—Ph-4-F) | CH₃ | |
| 5.18 | Cl | O—Ph-4-Ph | CH₃ | |
| 5.19 | Br | O—Ph-4-Ph | CH₃ | |
| 5.20 | Br | O—Ph-4-(O—Ph-4-F) | CH₃ | |
| 5.21 | Br | O—Ph-3-O—Ph | CH₃ | |
| 5.22 | Cl | O—Ph-4-Cl | Ph-4-CH₃ | |
| 5.23 | Cl | O—Ph-4-OC₂H₅ | CH₃ | |
| 5.24 | Cl | O—Ph-4-OCH₃ | CH₃ | |
| 5.25 | Cl | O—Ph-3.5-(OCH₃)₂ | CH₃ | |
| 5.26 | CH₃ | O—Ph-4-O—Ph | CH₃ | |

TABLE 5-continued

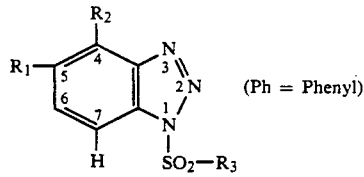
(Ph = Phenyl)

| Comp. No. | R₁ | R₂ | R₃ | Physical data |
|---|---|---|---|---|
| 5.27 | F | O—Ph-2-F | CH₃ | |

Formulation Examples for active ingredients of formula I (throughout, percentages are by weight)

| 2.1. Wettable powders | a) | b) | c) |
|---|---|---|---|
| a compound of the Tables | 25% | 50% | 75% |
| sodium lignosulfonate | 5% | 5% | — |
| sodium laurylsulfate | 3% | — | 5% |
| sodium diisobutylnaphthalenesulfonate | — | 6% | 10% |
| octylphenol polyethylene glycol ether (7–8 mol of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| 2.2. Emulsifiable concentrate | |
|---|---|
| a compound of the Tables | 10% |
| octylphenol polyethylene glycol ether (4–5 mol of ethylene oxide) | 3% |
| calcium dodecylbenzenesulfonate | 3% |
| castor oil polyglycol ether (35 mol of ethylene oxide) | 4% |
| cyclohexanone | 34% |
| xylene mixture | 50% |

Emulsions of any desired concentration can be obtained from this concentrate by dilution with water.

| 2.3. Dusts | a) | b) |
|---|---|---|
| a compound of the Tables | 5% | 8% |
| talcum | 95% | — |
| kaolin | — | 92% |

Ready-for-use dusts are obtained by mixing the active ingredient with the carrier and grinding the mixture in a suitable mill.

| 2.4. Extruder granules | |
|---|---|
| a compound of the Tables | 10% |
| sodium lignosulfonate | 2% |
| carboxymethylcellulose | 1% |
| kaolin | 87% |

The active ingredient is mixed and ground with the adjuvants, and the mixture is moistened with water. The mixture is extruded and then dried in a stream of air.

| 2.5. Coated granules |
|---|

| -continued | |
|---|---|
| a compound of the Tables | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granules are obtained in this manner.

| 2.6. Suspension concentrate | |
|---|---|
| a compound of the Tables | 40% |
| ethylene glycol | 10% |
| nonylphenol polyethylene glycol ether (15 mol of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

3. BIOLOGICAL EXAMPLES

Example 3.1

Action against Plasmopara viticola on vines a) Residual protective action

Vine seedlings in the 4-5 leaf stage are sprayed with a spray mixture (0.02% active ingredient) prepared from a wettable powder formulation of the test compound. After 24 hours the treated plants are infected with a sporangia suspension of the fungus. Fungus attack is evaluated after incubation for 6 days at 95-100% relative humidity and 20° C.

b) Residual curative action

Vine seedlings in the 4-5 leaf stage are infected with a sporangia suspension of the fungus. After incubation for 24 hours in a humidity chamber at 95-100% relative humidity and 20° C., the infected plants are dried and sprayed with a spray mixture (0.02% active ingredient) prepared from a wettable powder formulation of the test compound. After the spray coating has dried, the treated plants are again placed in the humidity chamber. Evaluation of fungus attack is made 6 days after infection.

Compounds of the Tables exhibit very good fungicidal activity against Plasmopara viticola on vines, and in particular compounds nos. 1.6, 1.13, 1.14, 1.16 and 1.30 inhibit fungus attack completely (0 to 5% residual attack). On the other hand, Plasmopara attack is 100% on untreated and infected control plants.

Example 3.2

Action against Phytophthora on tomato plants a) Residual protective action

After a cultivation period of 3 weeks, tomato plants are sprayed with a spray mixture (0.02% active ingredient) prepared from a wettable powder formulation of the test compound. After 24 hours the treated plants are infected with a sporangia suspension of the fungus. The infected plants are then incubated for 5 days at 90-100% relative humidity and 20° C. and then evaluated for fungus attack.

b) Systemic action

After a cultivation period of 3 weeks, a spray mixture (0.002% active ingredient, based on the volume of soil) prepared from a wettable powder formulation of the test compound is used to water tomato plants. Care is taken that the spray mixture does not come into contact with the parts of the plants above the soil. The treated plants are infected 48 hours later with a sporangia suspension of the fungus. The infected plants are then incubated for 5 days at 90-100% relative humidity and 20° C. and then evaluated for fungus attack.

Compounds of the Tables exhibit a lasting effect (less than 20% fungus attack). Compounds Nos. 1.3, 1.6, 1.13, 1.14, 1.16, 1.30 and 1.58 inhibit fungus attack almost completely (0 to 5% attack). On the other hand, Phytophthora attack is 100% on untreated and infected control plants.

Example 3.3

Action against Phytophthora on potato plants a) Residual protective action

After a cultivation period of 3 weeks, 2- to 3-week old potato plants (Bintje variety) are sprayed with a spray mixture (0.02% active ingredient) prepared from a wettable powder formulation of the test compound. The treated plants are infected 24 hours later with a sporangia suspension of the fungus. The infected plants are then incubated for 5 days at 90-100% relative humidity and 20° C. and then evaluated for fungus attack.

b) Systemic action

After a cultivation period of 3 weeks, a spray mixture (0.002% active ingredient, based on the volume of soil) prepared from a wettable powder formulation of the test compound, is used to water 2- to 3-week old potato plants (Bintje variety). Care is taken that the spray mixture does not come into contact with the parts of the plants above the soil. The treated plants are infected 48 hours later with a sporangia suspension of the fungus. The infected plants are then incubated for 5 days at 90-100% relative humidity and 20° C. and then evaluated for fungus attack.

Compounds of the Tables exhibit a lasting effect (less than 20% fungus attack). Compounds nos. 1.6, 1.13, 1.14, 1.30 and 1.58 inhibit fungus attack almost completely (0 to 5% attack). On the other hand, Phytophthora attack is 100% on untreated and infected control plants.

What is claimed is:

1. A compound of formula I

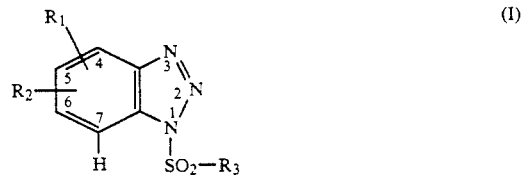

wherein:

$R_1$ is hydrogen, halogen, $C_1$-$C_4$alkyl, $C_1$-$C_4$alkoxy, $C_1$-$C_4$haloalkoxy having at least two identical or different halogen atoms, $CF_3$, nitro or the group $N(R')R''$, wherein $R'$ and $R''$ are each independently of the other $C_1$-$C_4$alkyl;

$R_2$ is phenoxy or phenylthio each of which is unsubstituted or mono-to tri-substituted by halogen, $C_1$-$C_4$alkyl, $C_1$-$C_4$alkoxy, $C_1$-$C_4$haloalkoxy hav-

23 ing at least two identical or different halogen atoms, cyano, nitro, $C_2$-$C_4$alkenyl, $C_2$-$C_4$alkynyl, phenyl, 2-phenylethynyl or by a further phenoxy radical that is unsubstituted or substituted by halogen, $C_1$-$C_4$alkyl and/or by $C_1$-$C_4$alkoxy; or $R_2$ is phenoxy which is substituted in the 3 and 4 positions by the radical —O—$CH_2$—O—;

$R_3$ is alkyl, aryl or aralkyl having a maximum of 14 carbon atoms, these radicals can be substituted by halogen, $C_1$-$C_4$alkyl and/or by nitro.

2. A compound according to claim 1 of formula I wherein: $R_1$ is hydrogen, halogen, $C_1$-$C_4$alkyl, methoxy, ethoxy, $CF_3$, $NO_2$, $C_1$-$C_2$haloalkoxy having at least two fluorine atoms, diethylamine or dimethylamine; and $R_2$ and $R_3$ are as defined for formula I.

3. A compound according to claim 2 of formula I wherein: $R_1$ is hydrogen, fluorine, chlorine, bromine, methyl, ethyl, methoxy, $CF_3$, $NO_2$, $C_1$-$C_2$haloalkoxy having at least 2 fluorine atoms, or dimethylamine; and $R_2$ and $R_3$ are as defined for formula I.

4. A compound according to claim 3 of formula I wherein: $R_1$ is hydrogen, chlorine, bromine, methyl, methoxy, $CF_3$, $NO_2$, trifluoromethoxy, trifluorochloroethoxy, difluoromethoxy or dimethylamine; and $R_2$ and $R_3$ are as defined for formula I.

5. A compound according to claim 4 of formula I wherein: R1 is chlorine, methyl, methoxy, $CF_3$ or dimethylamine; and $R_2$ and $R_3$ are as defined for formula I.

6. A compound according to claim 1 of formula I wherein: $R_2$ is phenoxy or phenylthio each of which is unsubstituted or mono- or di-substituted by fluorine, chlorine, bromine, $C_1$-$C_4$alkyl, $C_1$-$C_4$alkoxy, $C_1$-$C_2$haloalkoxy having at least 2 fluorine atoms, nitro, cyano, allyl, propargyl, 2-phenylethynyl or by a further phenoxy radical that is unsubstituted or substituted by fluorine, chlorine, bromine or by methyl; and $R_1$ and $R_3$ are as defined for formula I.

7. A compound according to claim 6 of formula I wherein: $R_2$ is phenoxy that is unsubstituted or substituted by fluorine, chlorine, bromine, $C_1$-$C_4$alkyl, $C_1$-$C_4$alkoxy, $C_1$-$C_2$haloalkoxy having at least 2 fluorine atoms, cyano, nitro, allyl, propargyl, 2-phenylethynyl or by a further phenoxy radical that is unsubstituted or substituted by fluorine, chlorine, bromine or by methyl; and $R_1$ and $R_3$ are as defined for formula I.

8. A compound according to claim 7 of formula I wherein: $R_2$ is phenylthio that is unsubstituted or substituted by fluorine, chlorine, $C_1$-$C_4$alkyl, $C_1$-$C_2$alkoxy, $C_1$-$C_2$haloalkoxy having at least 2 fluorine atoms, nitro, allyl, propargyl or by 2-phenylethynyl; and $R_1$ and $R_3$ are as defined for formula I.

9. A compound according to claim 8 of formula I wherein: $R_2$ is phenoxy that is unsubstituted or substituted by chlorine, bromine, methyl, tert-butyl, methoxy, ethoxy, trifluoromethoxy, cyano, nitro, allyl, propargyl, 2-phenylethynyl or by a further phenoxy radical that is unsubstituted or substituted by fluorine, bromine or by methyl; and $R_1$ and $R_3$ are as defined for formula I.

10. A compound according to claim 1 of formula I wherein: $R_3$ is $C_1$-$C_4$alkyl; $C_1$-$C_4$alkyl substituted by halogen; phenyl; phenyl substituted by halogen, $C_1$-$C_4$alkyl and/or by nitro; benzyl; or benzyl substituted by halogen, $C_1$-$C_4$alkyl and/or by nitro; and $R_1$ and $R_2$ are as defined for formula I.

11. A compound according to claim 10 of formula I wherein: $R_3$ is $C_1$-$C_4$alkyl; $C_1$-$C_4$alkyl substituted by fluorine or by chlorine; phenyl; phenyl substituted by chlorine, methyl or by nitro; benzyl; or benzyl substituted by chlorine, methyl or by nitro; and $R_1$ and $R_2$ are as defined for formula I.

12. A compound according to claim 1 of formula I wherein: $R_1$ is hydrogen, halogen, $C_1$-$C_4$alkyl, methoxy, ethoxy, $CF_3$, $NO_2$, $C_1$-$C_2$haloalkoxy having at least 2 fluorine and/or 2 chlorine atoms, diethylamine or dimethylamine;

$R_2$ is phenoxy or phenylthio each of which is unsubstituted or mono-or di-substituted by fluorine, chlorine, bromine, $C_1$-$C_4$alkyl, $C_1$-$C_4$alkoxy, $C_1$-$C_2$haloalkoxy having at least 2 fluorine atoms, cyano, nitro, allyl, propargyl, 2-phenylethynyl or by a further phenoxy radical that is unsubstituted or substituted by fluorine, chlorine, bromine or by methyl; and $R_3$ is $C_1$-$C_4$alkyl; $C_1$-$C_4$alkyl substituted by halogen; phenyl; phenyl substituted by halogen, $C_1$-$C_4$alkyl and/or by nitro; benzyl; or benzyl substituted by halogen, $C_1$-$C_4$alkyl and/or by nitro.

13. A compound according to claim 12 of formula I wherein: $R_1$ is hydrogen, fluorine, chlorine, bromine, methyl, ethyl, methoxy, $CF_3$, $NO_2$, $C_1$-$C_2$haloalkoxy having at least 2 fluorine atoms, or dimethylamine;

$R_2$ is phenoxy that is unsubstituted or substituted by fluorine, chlorine, bromine, $C_1$-$C_4$alkyl, $C_1$-$C_4$alkoxy, $C_1$-$C_2$haloalkoxy having at least 2 fluorine atoms, cyano, nitro, allyl, propargyl, 2-phenylethynyl or by a further phenoxy radical that is unsubstituted or substituted by fluorine, bromine or by methyl; and $R_3$ is $C_1$-$C_4$alkyl; $C_1$-$C_4$alkyl substututed by fluorine or by chlorine; phenyl; phenyl substituted by chlorine, methyl or by nitro; benzyl; or benzyl substituted by chlorine, methyl or by nitro.

14. A compound according to claim 13 of formula I wherein: $R_1$ is hydrogen, chlorine, bromine, methyl, methoxy, $CF_3$, $NO_2$, trifluoromethoxy, trifluorochloroethoxy, difluoromethoxy or dimethylamine;

$R_2$ is phenylthio that is unsubstituted or substituted by fluorine, chlorine, $C_1$-$C_2$alkyl, $C_1$-$C_2$alkoxy, $C_1$-$C_2$haloalkoxy having at least 2 fluorine atoms, nitro, allyl, propargyl or by 2-phenylethynyl; and $R_3$ is $C_1$-$C_4$alkyl; $C_1$-$C_4$alkyl substituted by fluorine or by chlorine; phenyl; phenyl substituted by chlorine, methyl or by nitro; benzyl; or benzyl substituted by chlorine, methyl or by nitro.

15. A compound according to claim 14 of formula I wherein: $R_1$ is chlorine, methyl, methoxy, $CF_3$ or dimethylamine;

$R_2$ is phenoxy that is unsubstituted or substituted by chlorine, bromine, methyl, tert-butyl, methoxy, ethoxy, trifluoromethoxy, cyano, nitro, allyl, propargyl, 2-phenylethynyl or by a further phenoxy radical that is unsubstituted or substituted by fluorine, bromine or by methyl; and $R_3$ is $C_1$-$C_4$alkyl; $C_1$-$C_4$alkyl substituted by fluorine or by chlorine; phenyl; phenyl substituted by chlorine, methyl or by nitro; benzyl; or benzyl substituted by chlorine, methyl or by nitro.

16. A compound of formula I according to claim 1 selected from the group consisting of:
1-N-methanesulfonyl-5-chloro-6-phenoxy-benzotriazole;
1-N-methanesulfonyl-5-chloro-6-(2-chlorophenoxy)-benzotriazole;
1-N-methanesulfonyl-5-chloro-6-(4-chlorophenoxy)-benzotriazole;

1-N-methanesulfonyl-5-chloro-6-(2,4-dibromo-
    phenoxy)-benzotriazole;
1-N-methanesulfonyl-5-chloro-6-(2-fluorophenoxy)-
    benzotriazole;
1-N-methanesulfonyl-5-chloro-6-(4-ethoxyphenoxy)-
    benzotriazole;
3-N-methanesulfonyl-5-chloro-6-phenoxy-benzo-
    triazole;
3-N-methanesulfonyl-5-chloro-6-(2-chlorophenoxy)-
    benzotriazole;
3-N-methanesulfonyl-5-chloro-6-(4-chlorophenoxy)-
    benzotriazole;
3-N-methanesulfonyl-5-chloro-6-(2,4-dibromo-
    phenoxy)-benzotriazole;
3-N-methanesulfonyl-5-chloro-6-(2-fluorophenoxy)-
    benzotriazole; and
3-N-methanesulfonyl-5-chloro-6-(4-ethoxyphenoxy)-
    benzotriazole;
and mixtures of the 1-N- and 3-N-substituted structural isomers.

17. A composition for controlling or preventing an attack by harmful microorganisms, which comprises a microbicidally effective amount of a compound or mixture of compounds of formula I

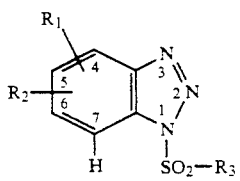

wherein:
R$_1$ is hydrogen, halogen, C$_1$–C$_4$alkyl, C$_1$–C$_4$alkoxy, C$_1$–C$_4$haloalkoxy having at least two identical or different halogen atoms, CF$_3$, nitro or the group N(R')R'', wherein R' and R'' are each independently of the other C$_1$–C$_4$alkyl;

R$_2$ is phenoxy or phenylthio each of which is unsubstituted or mono-to tri-substituted by halogen, C$_1$–C$_4$alkyl, C$_1$–C$_4$alkoxy, C$_1$–C$_4$haloalkoxy having at least two identical or different halogen atoms, cyano, nitro, C$_2$–C$_4$alkenyl, C$_2$–C$_4$alkynyl, phenyl, 2-phenylethynyl or by a further phenoxy radical that is unsubstituted or substituted by halogen, C$_1$–C$_4$alkyl and/or by C$_1$–C$_4$alkoxy; or R$_2$ is phenoxy which is substituted in the 3 and 4 positions by the radical —O—CH$_2$—O—;

R$_3$ is alkyl, aryl or aralkyl having a maximum of 14 carbon atoms, these radicals can be substituted by halogen, C$_1$–C$_4$alkyl and/or by nitro;
together with a suitable carrier.

18. A composition of claim 17 wherein R$_1$ is hydrogen, halogen, C$_1$–C$_4$alkyl, methoxy, ethoxy, CF$_3$, NO$_2$, C$_1$–C$_2$haloalkoxy having at least two fluorine atoms, diethylamine or dimethylamine.

19. A composition of claim 17 wherein
R$_1$ is hydrogen, halogen, C$_1$–C$_4$alkyl, methoxy, ethoxy, CF$_3$, NO$_2$, C$_1$–C$_2$haloalkoxy having at least 2 fluorine and/or 2 chlorine atoms, diethylamine or dimethylamine;

R$_2$ is phenoxy or phenylthio each of which is unsubstituted or mono-or di-substituted by fluorine, chlorine, bromine, C$_1$–C$_4$alkyl, C$_1$–C$_4$alkoxy, C$_1$–C$_2$haloalkoxy having at least 2 fluorine atoms, cyano, nitro, allyl, propargyl, 2-phenylethynyl or by a further phenoxy radical that is unsubstituted or substituted by fluorine, chlorine, bromine or by methyl; and R$_3$ is C$_1$–C$_4$alkyl; C$_1$–C$_4$alkyl substituted by halogen; phenyl; phenyl substituted by halogen, C$_1$–C$_4$alkyl and/or by nitro; benzyl; or benzyl substituted by halogen, C$_1$–C$_4$alkyl and/or by nitro.

20. A composition of claim 17 wherein the compound of formula I is selected from the group consisting of
1-N-methanesulfonyl-5-chloro-6-phenoxy-benzo-
    triazole;
1-N-methanesulfonyl-5-chloro-6-(2-chlorophenoxy)-
    benzotriazole;
1-N-methanesulfonyl-5-chloro-6-(4-chlorophenoxy)-
    benzotriazole;
1-N-methanesulfonyl-5-chloro-6-(2,4-dibromo-
    phenoxy)-benzotriazole;
1-N-methanesulfonyl-5-chloro-6-(2-fluorophenoxy)-
    benzotriazole;
1-N-methanesulfonyl-5-chloro-6-(4-ethoxyphenoxy)-
    benzotriazole;
3-N-methanesulfonyl-5-chloro-6-phenoxy-benzo-
    triazole;
3-N-methanesulfonyl-5-chloro-6-(2-chlorophenoxy)-
    benzotriazole;
3-N-methanesulfonyl-5-chloro-6-(4-chlorophenoxy)-
    benzotriazole;
3-N-methanesulfonyl-5-chloro-6-(2,4-dibromo-
    phenoxy)-benzotriazole;
3-N-methanesulfonyl-5-chloro-6-(2-fluorophenoxy)-
    benzotriazole; and
3-N-methanesulfonyl-5-chloro-6-(4-ethoxyphenoxy)-
    benzotriazole;
and mixtures of the 1-N- and 3-N-substituted structural isomers.

21. A method of controlling or preventing an attack on cultivated plants by phytopathogenic microorganisms, which comprises applying to the plants, parts of plants or the locus thereof, a microbicidally effective amount of a compound or mixture of compounds of formula I

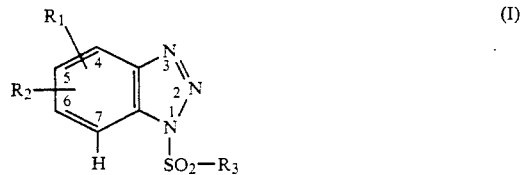

wherein:
R$_1$ is hydrogen, halogen, C$_1$–C$_4$alkyl, C$_1$–C$_4$alkoxy, C$_1$–C$_4$haloalkoxy having at least two identical or different halogen atoms, CF$_3$, nitro or the group N(R')R'', wherein R' and R'' are each independently of the other C$_1$–C$_4$alkyl;

R$_2$ is phenoxy or phenylthio each of which is unsubstituted or mono- to tri-substituted by halogen, C$_1$–C$_4$alkyl, C$_1$–C$_4$alkoxy, C$_1$–C$_4$haloalkoxy having at least two identical or different halogen atoms, cyano, nitro, C$_2$–C$_4$alkenyl, C$_2$–C$_4$alkynyl, phenyl, 2-phenylethynyl or by a further phenoxy radical that is unsubstituted or substituted by halogen, C$_1$–C$_4$alkyl and/or by C$_1$–C$_4$alkoxy; or R$_2$ is phenoxy which is substituted in the 3 and 4 positions by the radical —O—CH$_2$—O—;

R$_3$ is alkyl, aryl or aralkyl having a maximum of 14 carbon atoms, these radicals can be substituted by halogen, C$_1$–C$_4$alkyl and/or by nitro.

22. A method of claim 21 wherein $R_1$ is hydrogen, halogen, $C_1$-$C_4$alkyl, methoxy, ethoxy, $CF_3$, $NO_2$, $C_1$-$C_2$haloalkoxy having at least two fluorine atoms, diethylamine or dimethylamine.

23. A method according to claim 21, wherein phytopathogenic fungi are controlled.

24. A method according to claim 21, wherein the phytopathogenic fungi are Oomycetes.

25. A method according to claim 24, wherein the Oomycetes are the species Plasmopara and Phytophthora.